(12) United States Patent
Monroe (10) Patent No.: US 7,752,085 B2
(45) Date of Patent: Jul. 6, 2010

(54) PRODUCT INFORMATION MANAGEMENT SYSTEM

(75) Inventor: O. Napoleon Monroe, Huntington, NY (US)

(73) Assignee: Henry Schein, Inc., Melville, NY (US)

( * ) Notice: Subject to any disclaimer, the term of this patent is extended or adjusted under 35 U.S.C. 154(b) by 832 days.

(21) Appl. No.: 11/485,820

(22) Filed: Jul. 13, 2006

(65) Prior Publication Data

US 2008/0027997 A1 Jan. 31, 2008

(51) Int. Cl.
*G06F 17/30* (2006.01)
(52) U.S. Cl. .......................................... 705/27; 705/28
(58) Field of Classification Search ................... 705/26, 705/27
See application file for complete search history.

(56) References Cited

U.S. PATENT DOCUMENTS

| | | | |
|---|---|---|---|
| 4,658,830 | A | 4/1987 | Sarnoff |
| 4,862,896 | A | 9/1989 | Reinhold |
| 6,292,687 | B1 | 9/2001 | Lowell |
| 6,859,820 | B1 | 2/2005 | Hanuduc |
| 2003/0004946 | A1 | 1/2003 | VanDenAvond |
| 2003/0227392 | A1* | 12/2003 | Ebert et al. ............ 340/825.49 |
| 2003/0229543 | A1 | 12/2003 | Zimmerman |
| 2004/0046020 | A1* | 3/2004 | Andreasson et al. ........ 235/385 |
| 2004/0049428 | A1* | 3/2004 | Soehnlen et al. ............. 705/25 |

OTHER PUBLICATIONS

"Prescription Drug Marketing Act of 1987; Prescription Drug Amendments of 1992; Policies, Requirements and Administrative Procedures; Delay of Effective Date", Federal Register, vol. 69, No. 35, Feb. 23, 2004, pp. 8105-8107.

* cited by examiner

*Primary Examiner*—Robert M. Pond
(74) *Attorney, Agent, or Firm*—Brenda Pomerance (57) ABSTRACT

A product information tag, typically for a medical product such as a drug or device, is prepared in accordance with various rules. The product information tag is associated with the product as it travels from a product distributor to a shipper, to a customer such as a doctor and possibly even to a patient. When the product information tag is created, a database record for the product is also created. As the product passes into the possession of different parties, the database record is updated with information regarding the location and usage of the product. Different field devices, possessed by different parties such as the shipper or the doctor, are able to read the product information tag to obtain additional information relating to the product from the database and/or to provide supplemental information about the product to the database.

34 Claims, 8 Drawing Sheets

PRODUCT INFORMATION MANAGEMENT SYSTEM

BACKGROUND OF THE INVENTION

The present invention relates to managing product information, and more particularly, is directed to creating product information, including, in some cases, product tag information, to reflect the product's history and destination, and then updating the information to reflect product usage and exception events.

For medical products, such as pharmaceuticals and devices, some government regulations define information about the product as being part of the product. Regulations from different governments may conflict.

Certain government regulations further define the "label" for a medical product as comprising certain information affixed to the product's container as well as certain information accompanying the product, such as a written sheet with usage instructions or other information.

Government regulations for medical products differ by country, and may include requirements such as:
- making information available in Braille or audio for blind or partially-sighted customers,
- recording and reporting, within a first time period, of fatal or life-threatening experiences with the medical product,
- recording and reporting, within a second time period, of serious, unexpected, adverse experiences with the medical product,
- recording and reporting, within a third time period, of all adverse experiences with the medical product,
- storing, for a fourth time period, of all correspondence relating to experiences with the medical product, and
- ability to track a medical product through its life-cycle, defined as all or part of manufacturing, distribution and usage.

Further, a single medical product may be subject to different regulatory or procedural regimes, depending on how the product is used, e.g., given by a physician, or used by a consumer at home.

Best practices suggest that recording negative quality experiences, adverse reactions and other information associated with lot numbers or serial numbers helps focus quality initiatives.

In regions such as Europe, a medical products distributor may have to comply with preparing product labels in approximately 20 different languages.

A product distributor is a party other than the manufacturer, end user, or end user's medical services provider. Thus, a pharmacy can serve as a distributor.

Internet Publication http://www.devicelink.com/pmpn/archive/98/09/005.html discloses a medical packaging system for a medical products manufacturer, which utilizes a multilingual labeling sub-system in order to comply with European multiple-language labeling requirements. The sub-system scans a route sheet for a specific product code, and then compiles variable text, including language(s) for labels. A medical products manufacturer uses a language database, programs its printers to pull information from the database, and prints on packages produced from form-fill-seal machines.

It will be appreciated that the needs and capabilities of a manufacturer are different than those of a distributor.

For branded products from certain manufacturers that are distributed by multiple distributors, being able to prove that problem products were distributed by other than a specified distributor is of interest. Specifically, in products liability lawsuits where it is substantially impossible to prove which distributor distributed the problem products, it may be the case that liability is assigned to all distributors typically in proportion to their market share. Thus, the distributors with the largest market share have an interest in proving that the problem products came from distributors other than themselves.

U.S. Publication No. 20030229543 to Shannon M. Zimmerman et al. relates to centralized management of packaging data with rule-based content validation, which provides an online environment whereby manufacturers manage packaging data for their products. FIG. 14 illustrates translations data entry window 108E of user interface 101 that allows the user to select one or more languages 136 for translation and printing on a label of the packaging data. In this manner, any text printed on the label may be multilingual.

Another concern for medical products is that the device be properly programmed and used. For example, infusion pumps should be programmed to dispense the correct dose. At present, each device has its own user interface and terminology including dosing units. Further, nurses calibrate devices in different ways: manually, via monitors, or via the device itself. Some hospitals develop rule libraries of drug dosing units and dosage limits, and they load the rule libraries into the devices, along with actions required and/or suggested if something is out of range. It has been proposed to add monitoring and interruption capability to patient-controlled infusion devices.

Some medical devices are too small to have barcode labels affixed to the device. Affixing such labels particularly increases labeling, storage and transportation costs. Some small manufacturers are unwilling to invest in labeling systems to comply with lot and expiration barcode requirements, or affixing radio frequency identification (RFID) tags.

It is known to print information such as a bar code with electrically conductive ink. As used herein and in the claims, bar code refers to a conventional bar code, a data matrix, and techniques for representing printed information in condensed form relative to alphanumeric text.

Mobile communications have been proposed in the health area. SIMpill, a South African firm, makes a small device that clips on to a medication bottle and sends a text message to a central computer when the cap is removed. If no message arrives, the central computer sends a text message reminder to the patient's mobile phone.

As another example, LG, a South Korean handset manufacturer, sells a phone with a built-in blood glucose meter, for use by diabetics, that transmits readings to a computer for further analysis.

An example, from the automotive field, of transmitting sensor readings in conjunction with location is the General Motors OnStar system. Within seconds of a moderate to severe vehicle crash, the vehicle's OnStar module will send a message to the OnStar Call Center (OCC) through a cellular connection, informing an advisor at the call center that a crash has occurred. A voice connection between the advisor and the vehicle occupants is established. The advisor then can conference in 911 dispatch or a public safety answering point (PSAP), which determines if emergency services are necessary. If there is no response from the occupants, the advisor can provide the emergency dispatcher with the crash information from the vehicle's sensing and diagnostic module that reveals the severity of the crash. The dispatcher can identify what emergency services may be appropriate. Using the Global Positioning System (GPS) satellites, OnStar advisors are able to tell emergency workers the location of the vehicle.

It is expected that government regulations, the needs of customers for more information, as well as the desire to provide more features to customers, will result in increasing demands relating to the scope and availability of product information. For example, when customers can track their goods through the distribution process, the customers can treat distributor facilities as the customers' inventory warehouses.

Accordingly, there is room for an improved product information system.

SUMMARY OF THE INVENTION

In accordance with an aspect of this invention, there is provided a method of processing product related information, comprising storing original information relating to a product in a database record prior to distribution of the product by a product distributor, receiving additional information relating to the product after it has been distributed by the product distributor, storing the additional information in association with the original information in accordance with a product information tag accompanying the product, and producing a report based on the stored original information and the stored additional information.

In accordance with another aspect of this invention there is provided a method of using a product tag, comprising reading tag information from the product tag relating to the product, using the tag information to access a remote database containing stored information about the product, and providing the stored information for local access.

In accordance with a further aspect of this invention, there is provided a method of using a product tag, comprising reading tag information from the product tag relating to the product, collecting sensor information relating to the product, and transmitting the tag information and the sensor information to a remote database.

It is not intended that the invention be summarized here in its entirety. Rather, further features, aspects and advantages of the invention are set forth in or are apparent from the following description and drawings.

DETAILED DESCRIPTION

Figure 1:
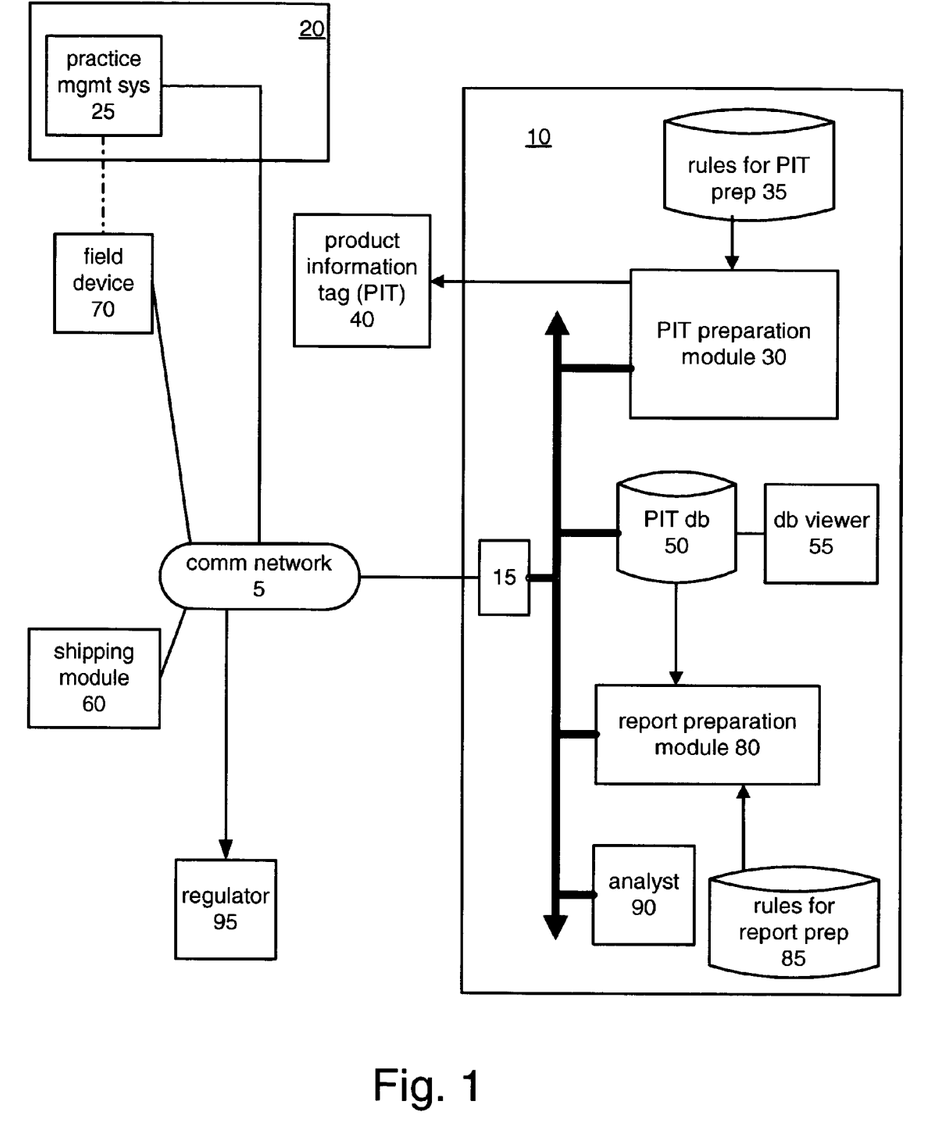
FIG. 1 is a block diagram showing product management system 10.

Referring now to the drawings, and in particular to FIG. 1, there are illustrated communication network 5, product management system 10, customer 20, customer practice management system 25, shipping module 60, field device 70 and regulator 95.

Communication network 5 may be any wireline or wireless network, such as the Internet, a private virtual network, a private dedicated network and so on. Further, communication network 5 may be embodied as a plurality of networks, for example, a wireline data network and a wireless voice network.

Product management system 10 includes communications interface 15, product information tag (PIT) preparation module 30, PIT preparation rules 35, PIT database 50, database viewer 55, report preparation module 80, report preparation rules 85, and analyst 90.

Product management system 10 is embodied as a general-purpose computer programmed in accordance with the present description. The general-purpose computer can be one computer or many computers networked together. System 10 can operate on dedicated or shared hardware, and may be at a user's premises or available as a so-called "web service" through communication network 5 or other communication facility. When system 10 is available as a web service, analyst 90 communications therewith via communication network 5, in similar manner as regulator 95.

Customer 20 is able to communicate with product management system 10 via communication network 5. In some embodiments, customer 20 has a general purpose computing device, such as a personal computer. In other embodiments, customer 20 has practice management system 25 which may be any conventional system for storing patient records, modified to also store PIT and other information described below, for example, the DENTRIX® system available from Henry Schein, Inc. A typical practice management system has a front-office portion for handling appointment scheduling and payments, a mid-office portion for handling patient records and a back-office portion for handling diagnostic and treatment information, as well as a patient portal enabling a patient to access their appointments and medical information via a communication network such as the Internet. In the examples described below, it is contemplated that information associated with products by a products distributor is captured by practice management system 25 and associated with the appropriate patient record.

In some embodiments, practice management system 25 uses communication network 5 to provide information to product management system 10, such as product usage and location information, and/or to receive information from product management system 10, such as recommended operating instructions and product supply chain information.

PIT preparation module 30 is adapted to generate PITs for products in accordance with customer order 20 and PIT preparation rules 35. Products typically are medical or pharmaceutical supplies, such as drugs or devices.

As used herein and in the claims, "PIT" means a record relating to a product that logically accompanies the product, and that may or may not physically accompany the product in whole or in part. In contrast, a "label", as the term is customarily used in the medical products industry, must physically accompany the product and include required standardized information.

A PIT may be embodied in any of the following ways: (a) as a printed paper affixed to a product or a product's container, (b) as a printed paper accompanying a product, (c) as an electromagnetic device affixed to or accompanying a product that stores information, (d) as an electromagnetic device affixed to or accompanying a product that enables access to information stored about the product, the information being stored in other than the electronic device that serves as the PIT, (e) combinations of the above, or (f) other configurations apparent to one of ordinary skill. Thus, a PIT may be information associated with a paper, such as a bar code, and/or information associated with an electronic or magnetic device.

Electronic devices suitable for a PIT include a radio frequency identification (RFID) tag, a "smart card" typically comprising a credit-card sized device with a processor and memory, a pattern that is magnetically readable as a bar code, and other devices that will be apparent to those of ordinary skill in the art.

Generally, the PIT serves to uniquely identify the product relative to other products in PIT database 50.

Customer 20 provides an order that typically includes identification of the desired product, quantity, a ship-to address, an order date and sometimes a delivery date and/or other special instructions. The instructions may be provided directly or indirectly. An example of indirect instructions is when a customer is in a country whose regulations stipulate certain requirements; the customer is deemed to have indirectly provided the certain requirements. The customer order may specify features of the product, for example, the type of container, and optional features such as stickers for patient charts, the stickers bearing product-related information.

PIT preparation rules 35 include product handling information based on the type of product, e.g., refrigerated, customer predefined preferences, shipping company requirements, regulatory requirements in the country of origin, regulatory requirements in the destination country, destination country characteristics such as official language(s), customs requirements, and special instructions in or related to the customer order.

The information in PIT preparation rules 35 relates to:
package layout and appearance;
what type of PIT should be used, i.e., sticker on product, product insert, electronic tag, bar code;
what historical information about the product content must be on its PIT: lot code, manufacturer date, serial number, UPC code and so on;
PIT information for the product container: whether refrigerated shipping is needed, individual container, package container, carton container, shipping pallet and so on;
associated products, e.g., syringes for fluids;
product trademark requirements;
promotional materials;
advice to include restrictions to be applied (ex: how to use, how to distribute, how to store);
whether a sensor is to be applied, and what type sensor may be appropriate; and
information related to communicating post-shipment information, such as if a product complaint has to be forwarded within a predetermined number of days after the complaint is received, if the complaint should generate a warning message or a reminder to appropriate parties such as the manufacturer.

For example, let it be assumed that the customer order specifies that 100 units of high speed dental operatory handpieces are to be sent to a location in Moldova and are to have RFHD tags with serial numbers. PIT preparation rules 35 specify that Moldova requires medical device instructions to be in Russian and in French, that the manufacturer of such handpiece as identified under Moldovian regulations be determinable, although not necessarily from the product PIT; that the customer wants its instruction sheets to have its name on the sheets, and the instructions in German and English, and its name affixed to the product itself; and that the regulatory requirements for Korea, the country of manufacture, specify that the date of manufacture must be on the PIT for the device.

In this example, PIT preparation module 30 creates PITs having stickers to be affixed to the handpieces having the customer name and the date of manufacture, creates inserts on paper having instructions for use in Russian, French, German and English, and creates RFID tags to be affixed to the handpieces containing the serial number of the respective handpieces.

When PIT preparation module 30 generates PIT 40, it also generates a PIT record and places the PIT record in PIT database 50. The PIT record includes at least the information provided in the PIT, and typically includes additional information. The PIT record serves as an audit trail for the past, present and future information about the product. Generally, the past information refers to the manufacturing history of the product, including manufacturer, product type, product serial number and UPC code, product version number, manufacture date, expiration date (if any), previous owners of the product, whether the product has been subject to recalls and field corrective actions, the number of previous sterilization procedures, extremes in storage conditions, and so on. The present information refers to instructions for use, which can be in one or more languages, or contain one or more pointers to instructional language, the present location of the product, and so on. The future information refers to the customer, the product's actual use, the shipper, the shipment route (if appropriate) and so on.

Supply chain information refers to information relating to how a product arrived at its current location, particularly, who had possession of the product, when, and the conditions experienced by the product while in a party's possession, such as ambient temperature and humidity ranges. A location sensing system, such as the global positioning system (GPS), can be a source of supply chain information.

In some embodiments, the PIT record includes information provided to the customer, as well as information provided from the customer, or the product itself while in the customer's possession.

During the lifetime of the product, the definition of present and future adapts. That is, after the product is received by the customer, the shipper becomes part of the past information. Usage and exception reports are then provided by the customer and/or the product, as discussed below.

Database viewer 55 enables a person, such as analyst 90, to view the contents of PIT database 50. Database viewer 55 is embodied as software for interacting with PIT database 50. Analyst 90 represents and suitable hardware for enabling a person to view information, such as a terminal or personal computer and/or printer. Database viewer 55 typically enables analyst 90 to formulate queries and apply them to PIT database 50. Many commercial database packages are known and suitable, such as Microsoft Access, MySQL, Oracle and so on.

PIT database 50 may be used for the following purposes:
to provide information to manufacturers for sales programs and recalls,
to provide information for product liability lawsuits quantifying the amount of product from a particular products distributor involved in malfunctions and the like,
for data mining,
to project product failure rates and the need to replace the product and/or maintain an inventory of spare replacement parts, to indicate which customers to focus on based on the customer's activity with regard to various procedures,
to recommend complementary or substitute products,
to provide different levels of customer support depending on the value of the customer,
to help decide where to locate sales and/or service centers, typically near the most frequent users of products.

Shipping module 60 enables the shipping service to update the PIT record, to indicate the present location of the product. Package tracking services are well known, and employed by, for example, UPS, Federal Express and the United States Post Office. In some embodiments, shipping module 60 is part of system 10, and queries the shipper's package tracking service for the status of products in transit. Shipping module enables a person or system associated with a shipping service to update the PIT record. Additionally, if a shipper has field device 70, PIT 40 may update the PIT record.

Field device 70 enables a customer or other authorized party to access a PIT record, and to update a PIT record with usage and exception information. Each PIT record may contain not only actual product usage information, but also supply chain information for the product. In some embodiments, field device 70 also transmits PIT and possibly other information directly to practice management system 25, so that the PIT and other information can be associated with patient records, enabling a patient record to directly provide product supply chain information. FIGS. 2A-2F show embodiments of field device 70.

Field device 70 can be located at any point along the product supply chain, including shipper premises, doctor premises and patient premises.

Usage information refers to customary activity that the product is involved in. For example, if the product is a device or medicine, the fact that it was subjected to temperatures above a first threshold or below a second threshold at any time is a usage event. If the product is a medicine, the fact that it was used (ingested, applied, etc.) by a patient on a certain date and time is a usage event. Lack of usage is also a form of usage information. Another example of a usage event is being dropped.

Exception information relates to an abnormal event associated with the product. For example, if the product is a device, a device failure is an exception event. If the product is a medicine, a side-effect in the patient, such as an allergic reaction, is an exception event.

In a simple case, the customer submits a usage and/or exception event via a written or faxed letter, possibly using a form.

Figure 2A:
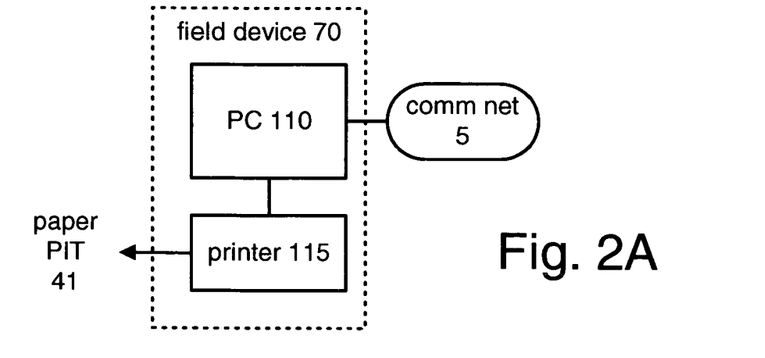
FIGS. 2A-2F are block diagrams showing embodiments of field device 70.

FIG. 2A shows field device 70 as comprising customer personal computer (PC) 110 and printer 115. Here, the customer communicates with PIT database 50 via electronic mail, or via a website. In some cases, the product PIT may need to be updated, and the updating occurs using printer 115. It will be appreciated that PC 110 may be a desktop, laptop, tablet or handheld personal computer, or a personal digital assistant, or even a cellular telephone with suitable processing ability.

Field device 70 is shown coupled to communication network 5. It will be understood that this coupling represents a path to a central computer, such as product management system 10, and/or, in some embodiments, to a local computer such as practice management system 25.

Figure 2B:
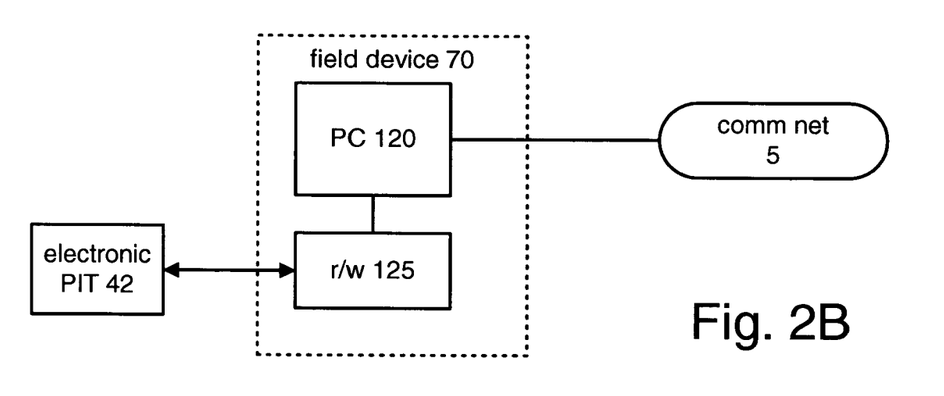

FIG. 2B shows field device 70 as comprising customer PC 120 and reader/writer 125. Here, the product bears or is associated with electronic PIT 42, such as an RFID tag or smart card. Reader/writer 125 reads information from electronic PIT 42, and passes the read information to PC 120, which in turn uses the read information to access the desired PIT record from PIT database 50. When PC 120 updates the PIT record, PIT database 50, or a program running in PC 120, may update electronic PIT 42 accordingly.

Figure 2C:
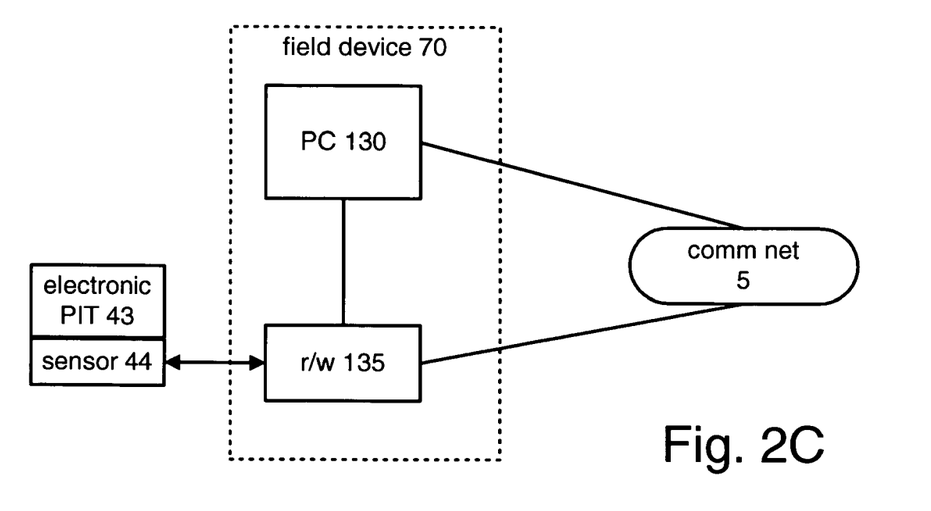

FIG. 2C shows field device 70 as comprising PC 130 and reader/writer 135. PC 130 and reader/writer 125 can communicate with each other, and each can communicate directly with PIT database 50. Here, the product bears or is associated with electronic PIT 43 and sensor(s) 44. Sensor 44 is adapted to detect regular usage events and some exception events, and to provide this information to electronic PIT 43. In some embodiments, sensor 44 also provides detected usage events and exception events directly to PIT database 50, for example, via wireless communication or via daily "synchronization" sessions or via as-needed synchronization sessions. In a synchronization session, the product communicates with PIT database 50, generally to provide information to PIT database 50. PC 130 is able to query PIT database 50, and also to report usage and/or exception events that are beyond the capability of sensor 44.

For example, if the product is a dental handpiece for holding drill bits, also referred to as burrs, sensor 44 may detect temperatures over a high threshold, such as 220° F., indicating that the handpiece has been subjected to a sterilization procedure; and also may detect temperatures under a low threshold, such as 40° F., indicating that the handpiece has been subjected to a lubrication procedure. That is, handpiece lubrication is often performed using a spray having a propellant that creates low temperatures.

As another example, high value implants such as heart pacemakers, titanium posts screwed into bones, dental implants, artificial knees and the like may have an embedded sensor that can be wirelessly read, in combination with a product information tag, to provide device status.

Figure 2D:
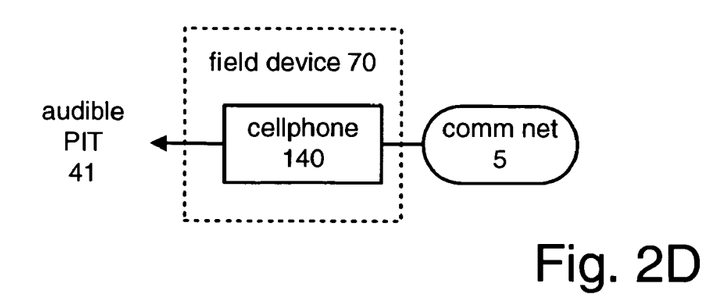

FIG. 2D shows field device 70 as comprising cellphone 140. Here, the customer uses cellphone 140 to call system 10 and verbally inquire about the PIT record and/or verbally provide a usage and/or exception event. Security measures may be employed, such as ensuring that the calling customer is actually the customer to whom the product was shipped.

Figure 2E:
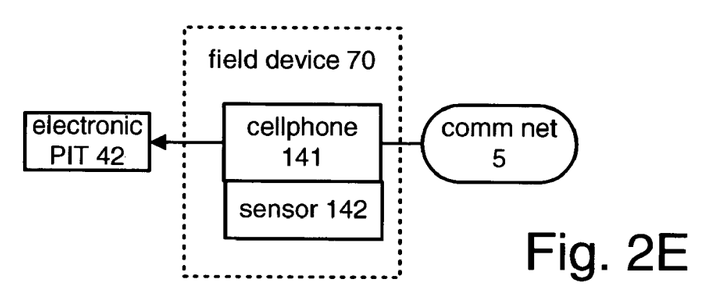

FIG. 2E shows field device 70 comprising cellphone 141 and sensor 142 that automatically places a call to provide sensed information. In other embodiments (not shown) field device 70 comprises a multi-media device, able to send and receive video and audio information, and also data, and possibly able to print data. When field device 70 is a multi-media device, the PIT information may comprise multi-media. For example, the usage instructions may be a video with closed-caption text and audio, explaining how to use the medical product. This form of presentation is particularly helpful for handicapped and/or illiterate people.

Field device 70 may be a programmable infusion pump for providing a drug. Typically, an infusion pump is programmed to provide a quantity of drug based on the bodyweight of the patient, sometimes with the ability for a patient to manually request more drug up to a predetermined maximum amount. The usage pattern of this device, combining its programming and the patient's manual requests, can be captured as part of a clinical trial, to correlate usage to outcome.

Similarly, for a dental restoration (filling), the usage of a combination of devices, e.g., a desensitizer and a composite resin, can be correlated with the clinical record and the patient outcome, to identify best usage techniques.

Figure 2F:
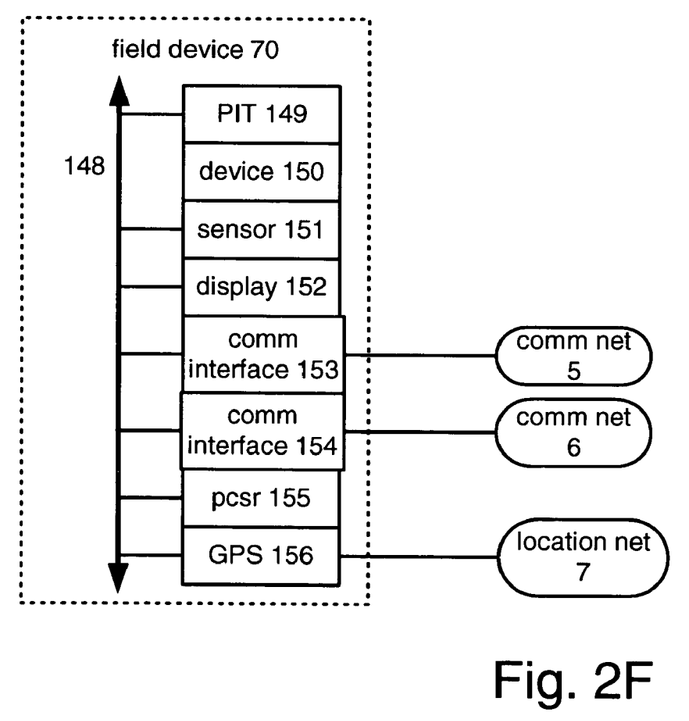

FIG. 2F shows field device 70 comprising internal communication network 148, PIT 149, device 150, sensor 151, display 152, remote interface 153, local interface 154, processor with memory 155, and location assembly 156. Internal communication network 148 may be a bus or a plurality of point-to-point connections. Sensor 151 senses at least one operating condition of device 150. In one instance, device 150 is a dental handpiece, and sensor 151 is a bimetallic sensor that disengages the chuck mechanism of the handpiece when a predetermined temperature is reached, to prevent overheating, as shown in more detail in FIG. 8A below. Audiovisual display 152 displays an indication of the operating condition of device 150 to its user, such as a dentist. When sensor 151 is triggered into sensing an event, either by usage of device 150 or by a poll received from remote interface 153 or local interface 154, sensor 151 activates location assembly 156 to communicate with location network 7, such as the global positioning system, to obtain the location of device 150 as a location stamp. Processor with memory 155 stores readings from sensor 151 in association with a time stamp and the location stamp, and provides the stored sensor readings and associated time stamp and location stamp to one or both of remote interface 153 and local interface 154, for transmission to product management system 10 and practice management system 25, via remote communication network 5 and local communication network 6, respectively.

Figure 11:
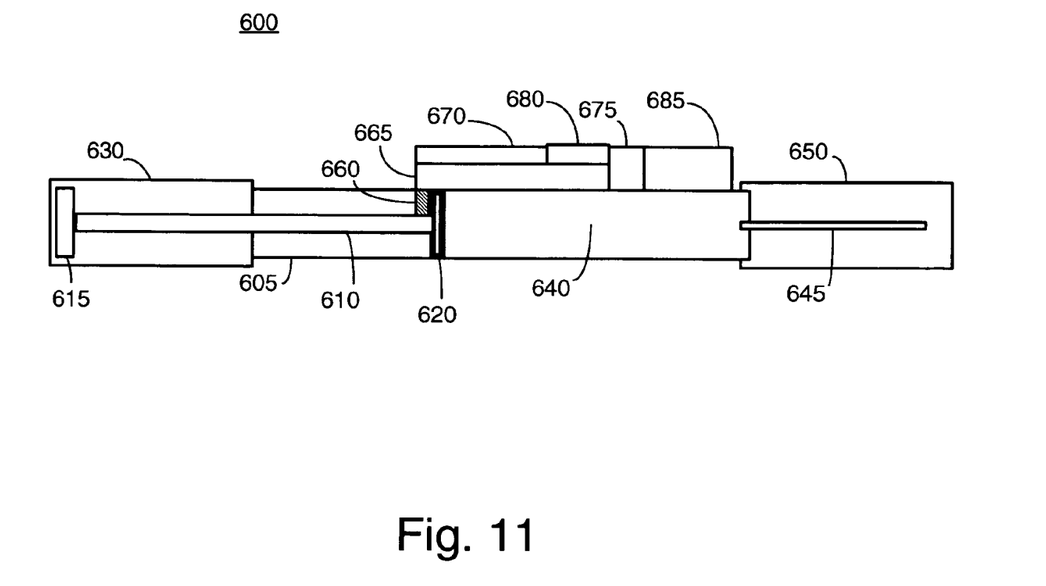
FIG. 11 is a view of an embodiment of an injector.

The device of FIG. 11 is an embodiment of the configuration of FIG. 2F.

In some embodiments, a biometric reader, such as a fingerprint reader, voice recognizer, retinal scanner or the like, is used to determine who is using device 150, and/or the identity of the patient receiving services via device 150. In other embodiments, a barcode scanner is used to input the identity of the user and/or patient. The identity information is typically associated with the PIT information in practice management system 25, but may be anonymized or absent from product management system 10 due to privacy concerns.

In some embodiments, interfaces 153, 154 and processor with memory 155 are in a cradle that device 150 having sensor 151 is placed into.

In combination with the PIT information, the sensor readings are analyzed to assess the cause for unexpected failure of a device or class of devices. Analysis occurs as product management system 10, practice management system 25, field device 70, or combinations thereof. A cause of failure may include usage patterns. Such assessment could be the basis for notifying the operator of a potential problem, offering maintenance training to operators predicting future product failures, and avoiding product liability.

One of the concerns of dentists in using certain light cured materials, such as material used to fill a tooth cavity, is the degree of cure accomplished during curing. To measure the amount of curing, a sensor is supplied with or built into the formulation of such light cured material.

An example of a sensor supplied with the material is a membrane radiometer placed proximal to the material, between the material on and/or in the tooth and the light source that measures the amount of light reaching the material, estimates therefrom the amount of curing and indicates when the estimated amount of curing (or amount of light) has reached a predetermined threshold. Another example of a sensor supplied with the material is an external transducer for measuring the hardness of the cured material.

An example of a sensor built into the light cured material is a material that changes color when a certain temperature is reached. Another example of a built-in sensor is a tiny transducer that measures pressure change, indicating the hardness of the cured material.

In some cases, multiple sensors are simultaneously operative. For example, device 150 may be a pouch that an instrument is placed into, and then the pouch is placed in a sterilization device, such as an autoclave, an oven or other device, to raise the contents of the pouch to a sterilization temperature. Here, the pouch has a sensor, the instrument has a sensor, and the sterilization device has a sensor. One example of a pouch sensor is an ink that changes color based on its temperature. Another example of a pouch sensor is a so-called indicator ink that changes color based on the amount of time it has been at or above a temperature threshold and a predefined relative humidity. Other example of pouch sensors are electronic, mechanical, or electromechanical device.

Figure 3:
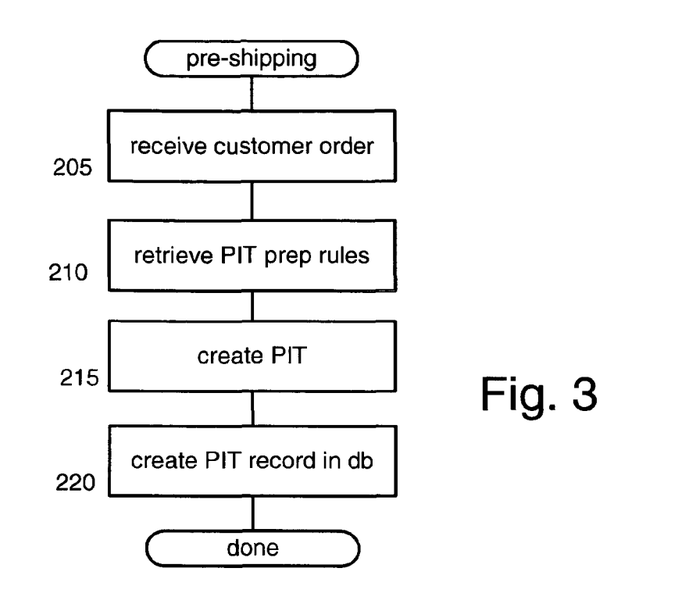
FIG. 3 is a flowchart showing pre-shipment processing.

FIG. 3 is a flowchart showing pre-shipment processing.

At step 205, a customer order is received. At step 210, PIT preparation module 30 retrieves PIT preparation rules from PIT preparation rules 35. At step 215, module 30 creates PITs in accordance with the customer order and PIT preparation rules. At step 220, module 30 creates a PIT record in PIT database 50.

Figure 4:
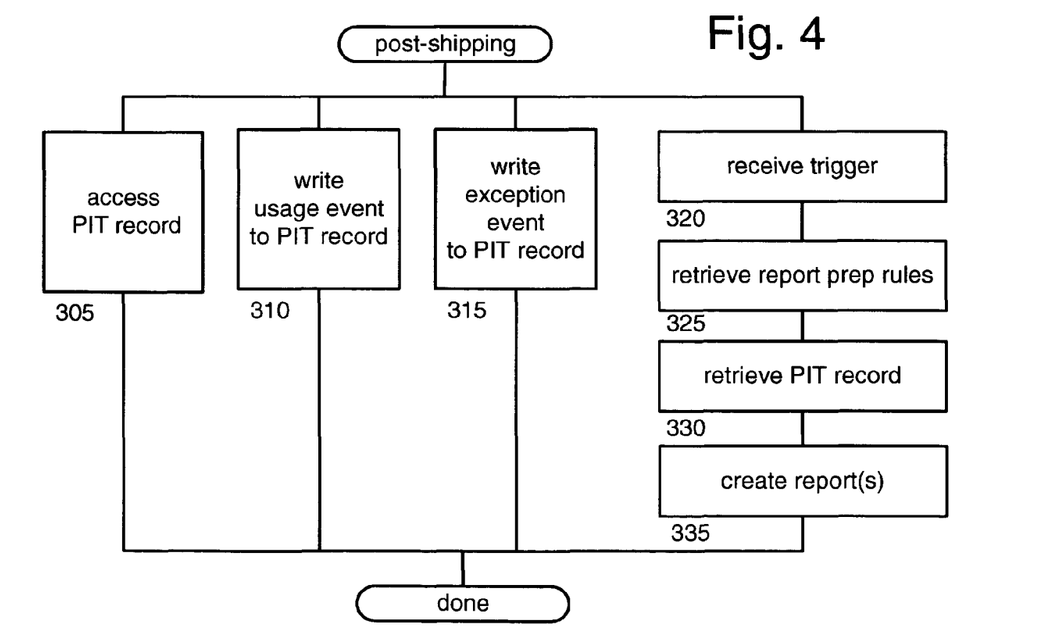
FIG. 4 is a flowchart showing post-shipment processing.

FIG. 4 is a flowchart showing post-shipment processing.

In one scenario, at step 305, a PIT record is accessed, via database viewer 55 or field device 70. The requested record is provided, and processing is complete.

In another scenario, at step 310, a usage event is written to a PIT record. The usage event may be provided via field device 70, or manual input (not shown) corresponding to the situations where the usage event is provided via telephone, fax or paper mail.

In another scenario, at step 315, an exception event is written to a PIT record. The exception event may be provided via field device 70, or manual input (not shown) corresponding to the situations where the exception event is provided via telephone, fax or paper mail.

In another scenario, at step 320, a trigger is received, such as a periodic trigger corresponding to time of day/week/month, or a one-time trigger corresponding to receipt of an exception event. At step 325, report preparation module 80 retrieves report preparation rules from report preparation rules 85. At step 330, module 80 retrieves one or more PIT records. At step 335, module 80 creates report(s) 90 in accordance with the PIT records and report preparation rules 85.

Report(s) 90 comprise:
- regulatory reports, such as reports of exception events, particularly adverse patient reactions, that may be electronically delivered to regulator 95,
- customer activity reports that are directed to how much and/or how often a product is being used, typically delivered to analyst 90,
- customer satisfaction reports that indicate problems and customer comments both good and bad, typically delivered to analyst 90, and
- re-order reports that are automatically generated as a product is used up or reaches the end of its lifetime and are electronically delivered to customer 20.

Report(s) 90 are based on data collected from and/or in association with PIT 40 while the product associated with PIT 40 is possessed by the product distribution, and other parties having possession of the product subsequent to the product distributor, including the shipper, the medical services provider such as doctor or dentist, and perhaps the ultimate patient.

To a distributor, an important piece of information is the customer's desire to reorder. Some distributors sell or supply scanners to customers, the scanners are for reading barcode labels identifying the products, so that reordering is accomplished via scanning. Typically, the barcode is unique to each manufacturer and carries the manufacturer's part number. Some distributors also affix their own bar code labels to a product, so that the product has two bar code labels, one from the manufacturer and the other from the distributor. In some cases, the customer, such as a large hospital chain or a dental school, may also affix its own bar code label to the product, so that the product has three bar code labels. Since the various bar code labels use different formats, depending on the source of the label, it is helpful to have an automated translation table between the various bar codes, to ensure, inter alia, that a product is properly recognized.

With suitable access authorization, analyst 90 can update PIT preparation rules 35 and report preparation rules 85.

A handpiece is a unit, typically used in the medical and dental professions, having a rapidly rotating member for altering the target, such as a patient's tooth, that is held in the hand of the party providing services to the target.

Figures 5A, 5B:
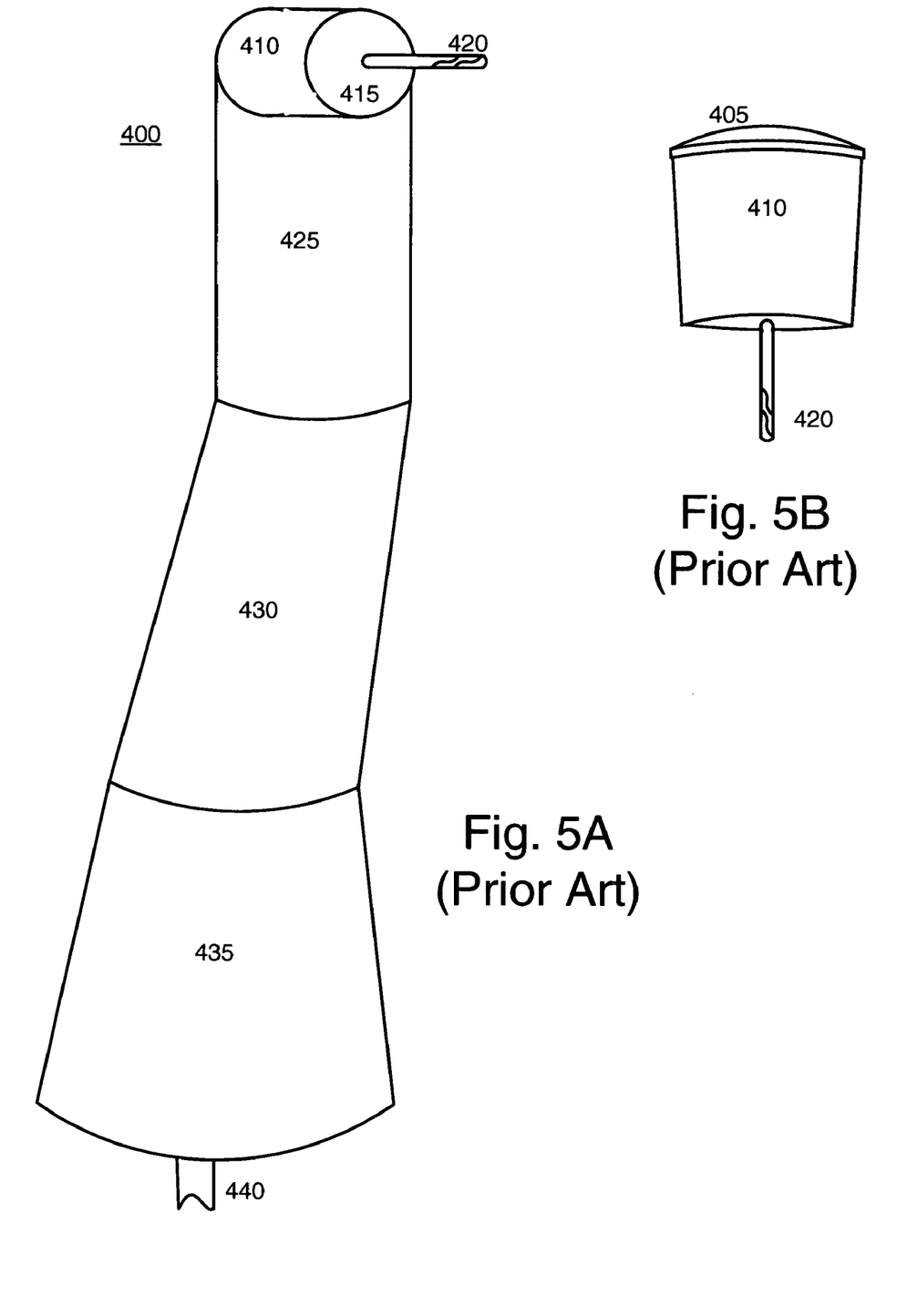
FIGS. 5A-5B are views of a conventional dental handpiece.

FIGS. 5A-5B show conventional dental handpiece 400 having head 410, stem 425, handle 430, base 435 and cord 440. Head 410 is generally in the shape of a cylinder having face 415 and push button 405 opposite face 415. Burr 420 is a removable drill bit inserted into the center of face 415. In operation, a dentist presses push button 415, causing power to be supplied via cord 440 to a turbine motor (not shown) inside head 410 that causes burr 420 to rotate at high speed. The turbine motor is supported by two doughnut shaped rings of bearings inside head 410. The bearing rings are respectively located towards the back and towards the front of head 410, surrounding the turbine.

One of the causes of failure of a handpiece is normal wear and tear. Another that one of the causes of failure of a handpiece is poor maintenance. In some cases, poor maintenance manifests itself by a change in the operating characteristics of the product. An example of this would be the build up of heat in handpieces which have not been properly cleaned and lubricated internally. With the movement of dental practitioners toward an electric rather than an air-powered handpiece, this maintenance becomes even more important. With an air-powered handpiece, an improperly maintained handpiece will simply stop working. With an electric-powered handpiece, the electric drive motor will continue to move the gears even though there is a build up of foreign material within the handpiece. The foreign material will cause friction and result in heat build up. It has been reported that this has caused temperatures to rise to the extent that patients have been injured. The repair cost of an electric-powered handpiece can be 5-20 times the cost of an air-powered handpiece.

Thus, measuring the heat of the turbine, and/or its vibration, is useful for detecting whether a handpiece is performing properly.

Figure 6A:
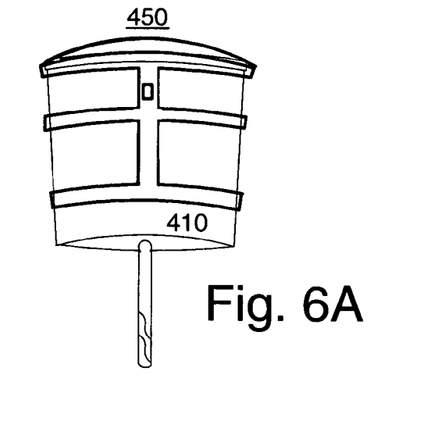
FIGS. 6A-6B are views of one embodiment of a clip-on girdle for a handpiece.
Figure 6B:
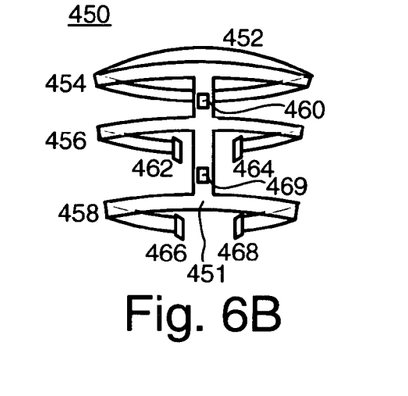

FIGS. 6A-6B are views of girdle 450 intended to clip on to handpiece 400, specifically, to wrap around handpiece head 410. Girdle 450 has spine 451, back support 454 having flexible membrane 452, back detection band 456 and front detection band 458. Detection band 456 has vibration sensor 462 at one end, and temperature sensor 464 at its other end. Detection band 458 has vibration sensor 466 at one end, and temperature sensor 468 at its other end. Sensors 462, 464, 466, 468 are generally in respective planes orthogonal to the planes of the ends of detection bands 458, 456; in some embodiments, the sensors are in the same plane as the detection bands. Spine 451 has product information tag 460 and sterilization sensor 469.

Girdle 450 may be formed of any suitable substance or combination of substances, such as a lightweight flexible metal for detection bands 456, 458, bimetallic material for sensors 464, 468 and piezoelectric material for vibration sensors 462, 466. Sterilization sensor 469 may be ink that changes color in response to temperature. Temperature sensors 464, 468 can change shape in response to temperature, as is typical for a bimetallic material, and/or can change color. Vibration sensors 462, 466 can change color in response to vibration.

Operation of girdle 450 will now be discussed.

Handpiece 400 is typically sterilized after each use. Similarly, girdle 450 is sterilized after each use, such as by putting girdle 450 in an autoclave or oven and raising the ambient temperature so that the temperature on the surface of girdle 450 reaches a predetermined temperature. Sterilization sensor 469, which may be printed ink that changes color when the predetermined temperature has been reached, serves to verify that sterilization of girdle 450 has occurred. Sterilization sensor 469 may be reset by applying pressure thereto.

After sterilization, girdle 450 is placed on head 410 so that flexible membrane 452 covers push button 405, back detection band 456 is generally over the back bearings ring, and front detection band 458 is generally over the front bearings ring.

Flexible membrane 452 enables the dentist to activate the turbine by pressing push button 405. Flexible membrane 452 may advantageously block some force applied to push button 405, such as when a dentist improperly rests push button 405 against a surface.

When handpiece 400 reaches a temperature above its normal operating temperature, the normal operating temperature being defined relative to each type of handpiece, the back of head 410 typically is hottest, and this temperature is picked up by back support 454 and communicated to detection bands 456, 458 via spine 451.

Detection band 456, being flexible, is responsive to the vibration and temperature caused by the back bearings ring. When the vibration of detection band 456 exceeds a first vibration threshold, vibration sensor 462 triggers, such as by changing shape or color. When the temperature of detection band 456 exceeds a first temperature threshold, temperature sensor 464 triggers, such as by changing shape or color. The triggering of a sensor indicates to the dentist that maintenance is needed.

Detection band 458 operates in similar manner as detection band 456, except that band 458 is responsive to the front bearings ring.

In some embodiments, the sensor triggering is communicated to product information tag 460 and/or a processor or controller, such as in FIG. 2C, via wireline or wireless communication. The processor can then cut off power to the handpiece to ensure that the handpiece is not permitted to operate while it is too hot.

Figure 7A:
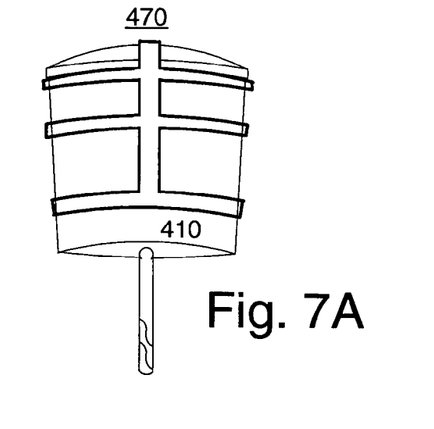
FIGS. 7A-7B are views of another embodiment of a clip-on girdle for a handpiece.
Figure 7B:
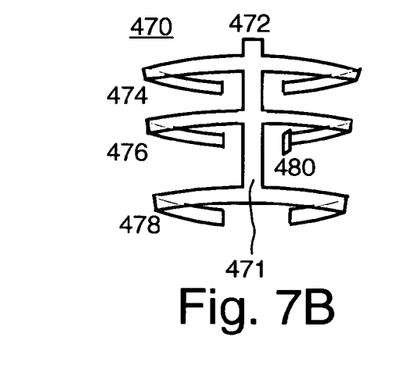

FIGS. 7A-7B are views of girdle 470, which is similar to girdle 450 except that girdle 470 has stabilizer clip 472 at its rear, instead of a flexible membrane, and has only one sensor.

Figure 8A:
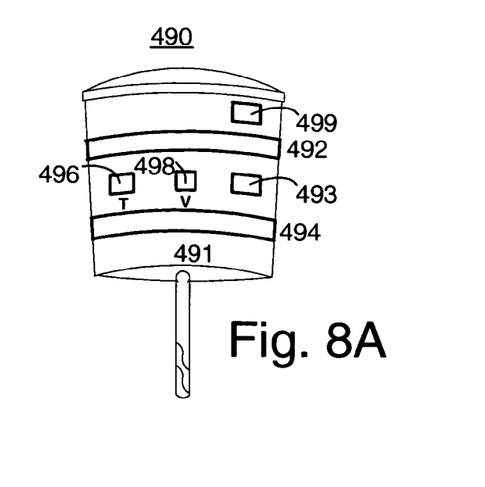
FIGS. 8A-8B are views of a handpiece according to the present invention.
Figure 8B:
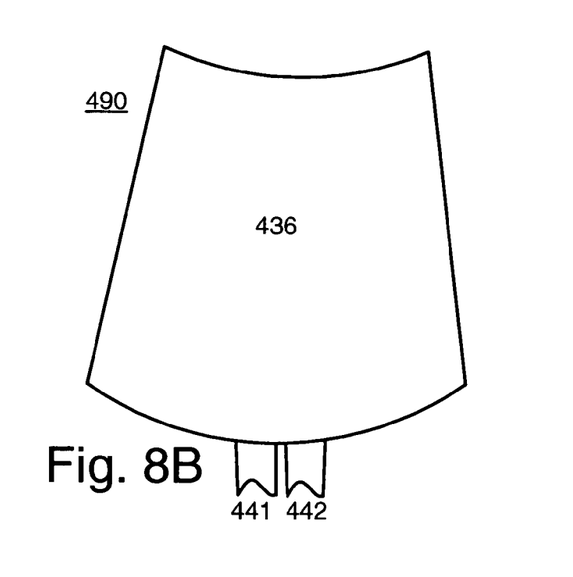

FIGS. 8A-8B are views of handpiece 490, which is generally similar to handpiece 400. For brevity, only the differences will now be discussed.

Handpiece 490 has head 491 having built-in detection bands 492, 494, product information tag 493, temperature indicator 496, vibration indicator 498, and sterilization indicator 499. Detection bands 492, 494 may be on the outside of head 491, the inside of head 491, or located in cut-out areas of head 491, as shown. Similar to detection bands 456, 458, detection bands 492, 494 respectively serve to detect temperature and vibration from the back and front bearing rings of handpiece 490. Respective temperature and vibration sensors, similar to those described above with respect to girdle 450, are located inside head 491, and cause indicators 496, 498 to light when appropriate thresholds are passed. Sterilization sensor 499 is similar to sterilization sensor 469 of girdle 450.

Handpiece 490 has base 436 having cords 441, 442 extending therefrom to a controller (not shown in FIGS. 8A-8B, but generally shown in FIG. 2C). Cord 441 provides power, similar to cord 440 of handpiece 400. Cord 442 provides electrical signals from the temperature and vibration sensors of head 491, and possibly signals to and from PIT 493, as generally shown in FIG. 2C. The controller is able to terminate power to the handpiece when the operating characteristics of the handpiece are deemed to be unacceptable.

In some embodiments, the sensors in handpiece 490 terminate power to the turbine when the appropriate thresholds are passed.

In some embodiments, the user of handpiece 490 is given the opportunity—but is not required—to indicate to the controller that usage instructions were read prior to use. The controller stores the indication, if provided, which is useful for subsequent investigations if a problem arises with the handpiece. In other embodiments, the controller requires that the user of handpiece 490 certify that usage instructions were read before enabling power to handpiece 490.

Figure 9A:
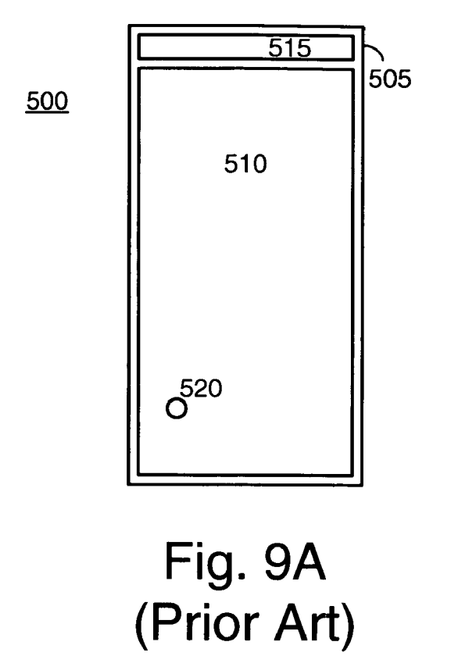
FIGS. 9A-9B are views of a conventional sterilization pouch.
Figure 9B:
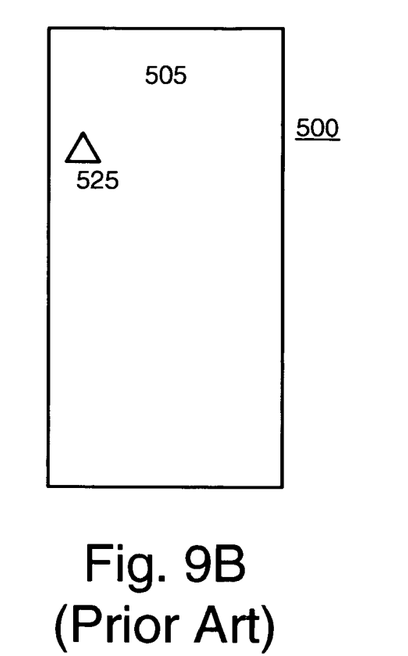

FIGS. 9A-9B are views of conventional sterilization pouch 500 having back 505, front 510 and adhesive strip 515. Typically, back 505 is formed of paper while front 510 is formed of transparent plastic. Front 510 is permanently affixed to back 505 along three edges. The unaffixed edge of front 510 is opposite adhesive strip 515. When the portion of back 505 bearing adhesive strip 515 is folded over the unaffixed edge of front 510, the unaffixed edge becomes affixed and a pouch is formed. Imprinted on the side of back 505 facing the pouch is temperature sensor 520, formed of thermally sensitive ink, which changes color when a predetermined temperature is reached. On the side of back 505 outside the pouch is sensor 525, formed of sensitive ink in a first color, which changes to a second color is the presence of chemical vapor or steam, and changes to a third color in the presence of ethylene oxide.

U.S. Pat. No. 5,344,017 shows another known sterilization pouch, in which the equivalent of sensor 520 is encased in a diamond shape formed by affixing the back to the front along lines forming a diamond.

Figure 10:
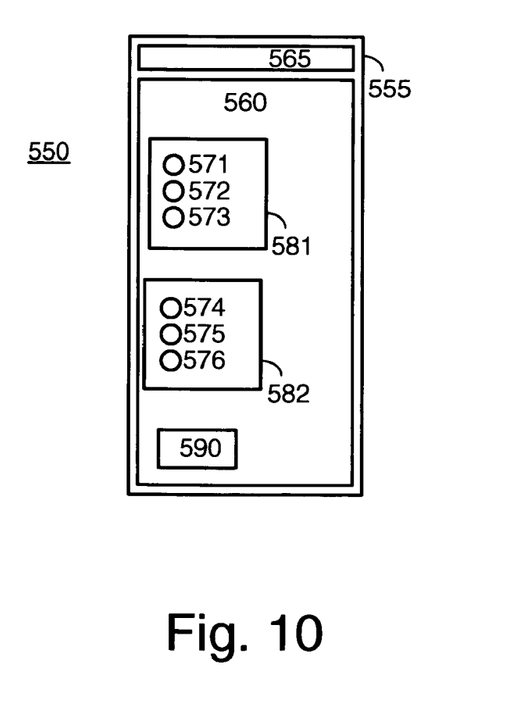
FIG. 10 is a view of an embodiment of a sterilization pouch.

FIG. 10 is a view of sterilization pouch 550. Sterilization pouch 550 is generally similar to pouch 500, and for brevity, only differences will be discussed.

Sterilization pouch 550 includes sensors 571, 572, 573 formed of thermally sensitive ink that changes color when different temperature thresholds $t_{571}$, $t_{572}$, $t_{573}$ are reached. Together, sensors 571, 572, 573 form an integrator. Sensors 571, 572, 572 are located behind panel 581, which ensures that the ink from the sensors does not contaminate the device being sterilized. In some embodiments, panel 581 is omitted. Panel 581 is typically transparent plastic.

Sterilization pouch 550 also includes sensors 574, 575, 576 that trigger when different temperature thresholds $t_{574}$, $t_{575}$, $t_{576}$ are reached. Sensors 574, 575, 578 are adapted to be read either electronically, magnetically or electromagnetically by an external sensor reader (see FIG. 2C). Sensors 574, 575, 578 are located behind panel 582, which ensures that the sensors remain separate from the device being sterilized.

Sterilization pouch 550 also includes PIT 590.

As used herein and in the claims, injector refers to a syringe or an auto-injector. A syringe is a device having a fluid and a hypodermic (hollow) needle wherein manual action of the user provides force for forcing the fluid through the hypodermic needle. An auto-injector is a device having a fluid, a spring and a hypodermic needle wherein the user merely places the uncapped device against his or her skin to release the spring that provides force for forcing the fluid through the hypodermic needle. Auto-injectors are well known, for example, U.S. Pat. Nos. 5,092,843 and 5,354,286, having a common inventor herewith, the disclosure of which is hereby incorporated by reference.

In some situations, such as exposure to bee stings for persons allergic thereto, or exposure to chemical agents, receiving an injection is critical for a person to stay alive. Chemical agents include nerve agents such as soman and sarin, biological agents, blood agents such as hydrogen cyanide, and other toxins. Persons at risk of such situations often carry an injector with them, since after realizing they have been exposed to danger, they have only a few moments of consciousness and so it is critical that an injector be nearby. In general, in a high threat situation with a rescue device, it is desirable for the rescue device, upon being used, to send a rescue signal indicating its location, so that rescue personnel can more readily know that their services are needed and find the harmed person. Additionally, for persons who should be carrying a rescue device, it may be desirable to remind such persons if their rescue device is not being carried.

FIG. 11 is a side view of injector 600. Injector 600 is shown as a syringe but, in other embodiments, is an auto-injector. When injector 600 is used to dispense its dosage, it determines its location, and sends a message to a central facility, such as a rescue center or product management system 10, giving its unique identification number and its location. The central facility uses the unique identification number to determine the contents of injector 600 and thus what sort of threat may have occurred so that suitable rescue personnel may be dispatched. The unique identification number may also be associated with a likely user of the device, and the user's organization may be notified that a problem has occurred and help is on its way. Injector 600 is an embodiment of the configuration of FIG. 2F.

Injector 600 includes housing 605, stem 610, plunger 615, movable disc 620, end cap 630, dosage chamber 640, hypodermic needle 645, needle cap 650, sensor 660, processor with memory 665, communications interface 670, PIT 675, battery 680 and location interface 685. Dosage chamber 640 is at least partially filled with rescue fluid.

When a user feels the need for rescue fluid, the user removes end cap 630 and needle cap 650 from injector 600, inserts needle 645 into the user's skin, then presses plunger 615 towards housing 605. The force applied to plunger 615 is transmitted to disc 620 via stem 610. The movement of disc 620 towards needle 645 forces the rescue fluid through needle 645 and into the user.

Usage of an auto-injector is described in U.S. Pat. Nos. 5,092,843 and 5,354,286.

Sensor 660 is inside housing 605, and is triggered by the movement of disc 620. In some embodiments, sensor 660 is triggered by the movement of stem 610. When sensor 660 triggers, it provides a signal to processor 665 via magnetic coupling or a physical contact made through a hole in the wall of housing 605. Processor 665 activates location interface 685 to obtain the location of injector 600, such as global positioning system (GPS) coordinates. Processor 665 then activates communication interface 670, such as by initiating a cellphone call to a predetermined telephone number associated with a central facility, and when communications are established, provides a unique identification number stored in PIT 675 along with the location from location interface 685 and possibly a timestamp. In some embodiments, instead of using a voiceband cellular channel, communication interface 670 uses an emergency frequency or a control channel or another wireless channel. Battery 680 can be in a standby or non-use state until sensor 660 is triggered, and only needs to provide power for the aforementioned activities, so battery 680 can be small.

In one case, disc 620 has a coating on its backside (side away from dosage chamber 640) that couples with sensor 660 to provide a first resistance to processor 665; when disc 620 is de-coupled from sensor 660 during use of injector 600, sensor 660 alone provides a second resistance to processor 665. The change in resistance, or the second resistance, seen by processor 665 serves as the trigger signal.

When the central facility is product management system 10, communication network 5 is the public switched telephone network coupled to the cellular telephone network that receives the call from processor 665 via communications interface 670. Communications interface 15 of product management system 10 serves to receive the call and store the event of the call in PIT database 50. PIT database 50 includes, in the record relating to the injector, the contents of the injector and an identity of a person having the injector. Rules database 85 includes a rule that when a call from injector 600 is received, an alert report is to be immediately prepared and delivered to analyst 90. In some embodiments, the rule or the database record relating to the injector specifies other parties that the alert report is to be delivered to, such as customer 20. Analyst 90 then arranges for dispatching of rescue personnel to the location of injector 600.

In some embodiments, injector 600 is configured so that the central facility is alerted when injector 600 is not being carried by the user, and can contact the user, such as by telephone or email, to remind the user to carry injector 600. As used herein and in the claims, detecting usage of an injector encompasses detecting when fluid is being forced through the injector's hypodermic needle, and detecting when the device is or is not being carried by the user.

In some cases, injector 600 periodically reports its location to the central facility, either by initiating a location transmission or responding to a location poll from the central facility. The central facility then compares at least two successive location reports to determine whether injector 600 is moving. Lack of motion indicates that the user might have forgotten to carry the injector.

In some cases, injector 600 periodically checks its location, stores its current location, and compares at least one of its stored previous locations with its current location, and notifies the central facility only if the comparison indicates no change, that is lack of motion.

With respect to movement detection, the location sensor can use GPS coordinates or can use a local metric, such as the position of a drop of fluid in a chamber, or any other metric that changes based on movement of the injector.

Although illustrative embodiments of the present invention, and various modifications thereof, have been described in detail herein with reference to the accompanying drawings, it is to be understood that the invention is not limited to these precise embodiments and the described modifications, and that various changes and further modifications may be effected therein by one skilled in the art without departing from the scope or spirit of the invention as defined in the appended claims.

What is claimed is:

1. A method of processing product related information, comprising:

creating a product information tag using a computer programmed with at least one product information tag preparation rule that specifies an action based on a customer order, the product information tag including identification information, associating the product information tag with a product received from a manufacturer, storing, using the computer, original information relating to the product in a database record of a database prior to distribution of the product by a product distributor, the database record associated with the identification information in the product information tag that accompanies the product, the identification information uniquely identifying the product in the database, receiving shipment information including an identity of a shipper and an environmental condition experienced by the product while in possession of the shipper, the shipment information accompanied by the identification information in the product information tag, storing, using the computer, the shipment information in association with the original information in the database, receiving usage information relating to use of the product, the usage information accompanied by the identification information in the product information tag, storing, using the computer, the usage information in association with the original information in the database, receiving exception information relating to an abnormal event associated with the product after the product has been distributed by the product distributor, the exception information accompanied by the identification information in the product information tag, storing, using the computer, the exception information in association with the original information in the database, and analyzing, using the computer, the exception information, and at least one of (a) the shipment information and (b) the usage information, to understand the cause of the abnormal event.

2. The method of claim 1, wherein the product is a drug or medical device.

3. The method of claim 1, wherein product information tag preparation rules relate to at least two of:
(a) package layout and appearance;
(b) what type of product tag should be used;
(c) what historical information about the product must be on its product tag;
(d) product tag information for the product container;
(e) associated products;
(f) product trademark requirements;
(g) promotional materials
(h) advice to include restrictions to be applied;
(i) whether a sensor is to be applied,
(j) what type sensor may be appropriate; and
(k) information related to communicating post-shipment information.

4. The method of claim 1, wherein the product is a device, and the exception information relates to a failure of the device.

5. The method of claim 1, wherein the product is a drug, and the exception information a side-effect experienced by a user of the drug.

6. The method of claim 1, wherein the usage information is received from a field device.

7. The method of claim 6, wherein the field device reads the identification information from the product information tag.

8. The method of claim 1, wherein the usage information is in accordance with sensor information from a sensor, the usage information relating to an operating condition of the product.

9. The method of claim 8, wherein the sensor is embedded in the product.

10. The method of claim 1, wherein the usage information is received from a practice management system.

11. The method of claim 1, further comprising producing a report based on the analysis of the exception information and at least one of the shipment information and the usage information.

12. The method of claim 11, further comprising transmitting the report to a practice management system.

13. The method of claim 1, wherein the database record is for storing at least three of:
   (a) the information provided in the product information tag,
   (b) the manufacturing history of the product,
   (c) manufacturer,
   (d) product type,
   (e) product serial number
   (f) product identifying code,
   (g) product version number,
   (h) manufacture date,
   (i) expiration date,
   (j) previous owners of the product,
   (k) recalls of the product,
   (l) field corrective actions of the product,
   (m) a number of previous sterilization procedures,
   (n) extreme values for storage conditions
   (o) instructions for use,
   (p) at least one pointer to an instructional language,
   (q) a present location of the product,
   (r) a customer identification,
   (s) actual use of the product,
   (t) a shipper of the product,
   (u) a shipment route of the product,
   (v) information for provision to a customer,
   (w) information received from a customer while the product is in the customer's possession, and
   (x) information received from the product information tag while the product is in the customer's possession.

14. The method of claim 1, wherein the original information includes customer order information including at least three of
   (a) a quantity,
   (b) a ship-to address,
   (c) an order date
   (d) a delivery date
   (e) special instructions
   (f) a feature of the product
   (g) a type of container,
   (h) a specification of accompanying printed information and optional features such as stickers for patient charts, the stickers bearing product-related information.

15. The method of claim 1, wherein the product information tag preparation rule embodies regulations of a country in a ship-to address in the customer order.

16. The method of claim 1, wherein the shipment information includes humidity information.

17. The method of claim 1, wherein shipment information includes timestamp information.

18. The method of claim 1, wherein the shipment information includes location information.

19. The method of claim 1, wherein the product information tag is one of
   (a) a printing affixed to the product or a container for the product,
   (b) a printed medium accompanying the product,
   (c) an electromagnetic device affixed to or accompanying the product, the electromagnetic device for storing information, and
   (d) an electromagnetic device affixed to or accompanying the product, the electromagnetic device for enabling access to the stored database record for the product.

20. The method of claim 19, wherein the electromagnetic device is one of
   (a) a radio frequency identification (RFID) tag,
   (b) a smart card, and
   (c) a pattern that is electromagnetically readable.

21. A method of processing product related information, comprising:
   associating a product information tag with a product received from a manufacturer, the product information tag having been created using at least one product information tag preparation rule that specifies an action based on a customer order, the product information tag including identification information,
   storing, using a computer, original information relating to the product in a database record of a database prior to distribution of the product by a product distributor, the database record associated with the identification information in the product information tag that accompanies the product, the identification information uniquely identifying the product in the database,
   receiving shipment information including an identity of a shipper and an environmental condition experienced by the product while in possession of the shipper, the shipment information accompanied by the identification information in the product information tag,
   storing, using the computer, the shipment information in association with the original information in the database,
   receiving usage information relating to use of the product, the usage information accompanied by the identification information in the product information tag,
   storing, using the computer, the usage information in association with the original information in the database,
   receiving exception information relating to an abnormal event associated with the product after the product has been distributed by the product distributor, the exception information accompanied by the identification information in the product information tag,
   storing, using the computer, the exception information in association with the original information in the database, and
   analyzing, using the computer, the exception information, and at least one of (a) the shipment information and (b) the usage information to understand the cause of the abnormal event,
   wherein at least one of the environmental condition information and the usage information is generated by a sensor embedded in the product.

22. The method of claim 21, wherein the product is a drug or medical device.

23. The method of claim 21, wherein the product is a device, and the exception information relates to a failure of the device.

24. The method of claim 21, wherein the product is a drug, and the exception information a side-effect experienced by a user of the drug.

25. The method of claim 21, wherein the usage information is received from a practice management system.

26. The method of claim 21, wherein the product information tag is one of
(a) a printing affixed to the product or a container for the product,
(b) a printed medium accompanying the product,
(c) an electromagnetic device affixed to or accompanying the product, the electromagnetic device for storing information, and
(d) an electromagnetic device affixed to or accompanying the product, the electromagnetic device for enabling access the stored database record for the product.

27. The method of claim 26, wherein the electromagnetic device is one of
(a) a radio frequency identification (RFID) tag,
(b) a smart card, and
(c) a pattern that is electromagnetically readable.

28. A machine for processing product related information, comprising:
a computer coupled to a memory, wherein the computer is programmed to process the product related information by
creating a product information tag using at least one product information tag preparation rule that specifies an action based on a customer order, the product information tag including identification information,
associating the product information tag with a product received from a manufacturer,
storing original information relating to the product in a database record of a database prior to distribution of the product by a product distributor, the database record associated with the identification information in the product information tag that accompanies the product, the identification information uniquely identifying the product in the database,
receiving shipment information including an identity of a shipper and an environmental condition experienced by the product while in possession of the shipper, the shipment information accompanied by the identification information in the product information tag,
storing the shipment information in association with the original information in the database,
receiving usage information relating to use of the product, the usage information accompanied by the identification information in the product information tag,
storing the usage information in association with the original information in the database,
receiving exception information relating to an abnormal event associated with the product after the product has been distributed by the product distributor, the exception information accompanied by the identification information in the product information tag,
storing the additional exception information in association with the original information in the database, and
analyzing the exception information, and at least one of (a) the shipment information and (b) the usage information, to understand the cause of the abnormal event.

29. The machine of claim 28, wherein the product is a drug or medical device.

30. The machine of claim 28, wherein the product is a device, and the exception information relates to a failure of the device.

31. The machine of claim 28, wherein the product is a drug, and the exception information a side-effect experienced by a user of the drug.

32. The machine of claim 28, wherein the usage information is received from a practice management system.

33. The machine of claim 28, wherein the product information tag is one of
(a) a printing affixed to the product or a container for the product,
(b) a printed medium accompanying the product,
(c) an electromagnetic device affixed to or accompanying the product, the electromagnetic device for storing information, and
(d) an electromagnetic device affixed to or accompanying the product, the electromagnetic device for enabling access to the stored database record for the product.

34. The machine of claim 33, wherein the electromagnetic device is one of
(a) a radio frequency identification (RFID) tag,
(b) a smart card, and
(c) a pattern that is electromagnetically readable.

* * * * *